(12) United States Patent
Dong et al.

(10) Patent No.: US 6,551,613 B1
(45) Date of Patent: *Apr. 22, 2003

(54) DOSAGE FORM COMPRISING THERAPEUTIC FORMULATION

(75) Inventors: Liang-Chang Dong, Sunnyvale, CA (US); Patrick S. L. Wong, Burlingame, CA (US); Vincent Joseph Ferrari, Foster City, CA (US); Steven Espinal, Mountain View, CA (US)

(73) Assignee: Alza Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/353,519

(22) Filed: Jul. 14, 1999

Related U.S. Application Data

(60) Provisional application No. 60/099,401, filed on Sep. 8, 1998.

(51) Int. Cl.[7] .............................. A61K 9/48; A61K 9/64; A61K 9/66; A61K 9/24; A61F 13/00
(52) U.S. Cl. ...................... 424/451; 424/422; 424/455; 424/456; 424/457; 424/473
(58) Field of Search ................................ 424/422, 451, 424/455, 456, 457, 473

(56) References Cited

U.S. PATENT DOCUMENTS

| | | | |
|---|---|---|---|
| 3,133,132 A | 5/1964 | Loeb et al. | 264/49 |
| 3,173,876 A | 3/1965 | Zobrist | 252/137 |
| 3,276,586 A | 10/1966 | Rosaen | 210/90 |
| 3,541,005 A | 11/1970 | Strathmann et al. | 210/19 |
| 3,541,006 A | 11/1970 | Bixler et al. | 210/23 |
| 3,546,142 A | 12/1970 | Michaels et al. | 260/2.1 |
| 3,845,770 A | 11/1974 | Theeuwes et al. | 128/260 |
| 3,905,360 A | 9/1975 | Zaffaroni | 128/130 |
| 3,916,899 A | 11/1975 | Theeuwes et al. | 128/260 |
| 4,077,407 A | 3/1978 | Theeuwes et al. | 128/260 |
| 4,111,201 A | 9/1978 | Theeuwes | 128/260 |
| 4,160,020 A | 7/1979 | Ayer et al. | 424/15 |
| 4,259,323 A | 3/1981 | Ranucci | 424/153 |
| 4,627,850 A | * 12/1986 | Deters et al. | 604/892 |
| 4,853,229 A | * 8/1989 | Theeuwes | 424/455 |
| 4,951,494 A | 8/1990 | D'Alterio | 72/199 |
| 5,391,381 A | * 2/1995 | Wong et al. | 424/473 |
| 5,531,736 A | * 7/1996 | Wong et al. | 604/892.1 |
| 5,614,578 A | 3/1997 | Dong et al. | 524/377 |
| 5,620,705 A | 4/1997 | Dong et al. | 424/472 |
| 5,965,160 A | * 10/1999 | Benita et al. | 424/455 |
| 6,087,353 A | * 7/2000 | Stewart et al. | 514/182 |
| 6,200,600 B1 | * 3/2001 | Rashid | 424/451 |

FOREIGN PATENT DOCUMENTS

GB  2 155 899 A  10/1985  ............ A61K/9/48

OTHER PUBLICATIONS

Considine and Considine eds., Van Nostrand Reinhold Encyclopedia of Chemistry, pp 644–645, 1984.
Encyclopedia of Polymer Science and Technology vol. 3, pp 325–354, 1965.
Pharmaceutical Sciences by Remington, 17th ed, pp 403–405, 1985.
Clayton and Clayton eds., Patty's Industrial Hygiene and Toxicology, vol. 2C, pp 3844–3852 and pp 3901–3907, 1982.

* cited by examiner

*Primary Examiner*—Thurman K. Page
*Assistant Examiner*—S. Tran
(74) *Attorney, Agent, or Firm*—Robert R. Neller; Paul B. Simboli

(57) ABSTRACT

A dosage form is disclosed comprising a semipermeable walled container that houses a capsule, which capsule comprises a drug formulation, a piston, and an osmotic composition. The dosage form delivers the drug formulation through a passageway at a controlled rate over a sustained-release period of time up to 24 hours.

5 Claims, 2 Drawing Sheets

DOSAGE FORM COMPRISING THERAPEUTIC FORMULATION

RELATED APPLICATIONS

This application claims the benefit of U.S. Provisional Application No. 60/099,401 filed on Sep. 8, 1998.

FIELD OF THE INVENTION

The present invention pertains to both a useful dosage form and to the process of manufacturing the dosage form. More particularly, the invention relates to a dosage form comprising a wall that surrounds an internal compartment comprising a therapeutic formulation, a piston, a driving member, and a passageway for delivering the therapeutic formulation from the dosage form. The invention concerns also a process for manufacturing the dosage form comprising the steps of uniting the components of the dosage form into the manufactured dosage form. The invention relates also to a method of using the dosage form for dispensing the therapeutic formulation at a controlled rate over a sustained-release period of time.

BACKGROUND OF THE INVENTION

In the fields of pharmacy and medicine, many drugs are blended with a pharmaceutically acceptable carrier for administering to a patient. For example, many drugs are administered to a patient by dissolving the drug in an aqueous or in a nonaqueous pharmaceutically acceptable carrier, by suspending the drug in a pharmaceutically acceptable solvent, or by incorporating the drug into one of two phases of an acceptable oil and water system.

These pharmaceutical preparations are useful as they can be formulated for different routes of administration, including oral use, administering into body openings such as the vagina and anus, or applied topically. Their dose can be adjusted, and they can be administered to children and adults.

The preparation of these pharmaceutical preparations involves considerations on the part of the pharmacist, including the purpose of the drug, internal or external use, concentration of the drug, the pharmaceutical carrier, and other characteristics that lead to the final pharmaceutical preparation. However, there is serious shortcomings associated with these pharmaceutical preparations; mainly, the absence of a dosage form for administering the pharmaceutical preparations at a controlled rate over a sustained-release period for administering the drug for a therapeutic benefit.

It will be appreciated by those versed in the drug dispensing art in view of the above presentation, that if a dosage form is made available for delivering pharmaceutical formulations that overcomes tribulations of the prior art, such a dosage form would have a practical value in the drug dispensing art. Likewise, it will be scientifically self-evident to those versed in the drug delivery art, that if a dosage form is made available that can administered pharmaceutical formulations comprising the prescribed dose at a sustained-release and controlled rate, such an unexpected dosage form would have an immediate acceptance for positive therapy in both human and veterinary medicine.

OBJECTS OF THE INVENTION

Accordingly, in view of the above presentation it is an immediate object of the invention to provide a dosage form that can deliver a pharmaceutical formulation and thereby overcome the tribulations of the prior art.

Yet another object of the invention is to provide a dosage form that can deliver a pharmaceutical formulation at a sustained-release and controlled rate over an extended time.

Yet another object of this invention is to provide a dosage form that can deliver an initially dry pharmaceutical formulations that converts to a liquid pharmaceutical formulation in the dosage form during the use of the dosage form in a liquid environment of use.

Another object of the invention is to provide a dosage form comprising an internal capsule which comprises a liquid formulation containing a drug and a separate layer possessing expansion properties.

Another object of the invention is to provide a dosage form comprising a nonaqeous liquid formulation comprising an orally administrable drug that can deliver a prescribed dose of drug to a patient in need of therapy.

Another object of the invention is to provide a dosage form comprising a liquid formulation containing a liquid soluble drug that can be dispensed in a known dose for a therapeutic benefit.

Another object of the invention is to provide a dosage form comprising a capsule containing a nonaqueous liquid in which a protein or proteinaceous drug is dissolved or dispersed for sustained-lase administration at a by controlled rate over time.

Another object of the invention is to provide a dosage form comprising a capsule that contains an emulsion-drug composition that can be delivered at a controlled rate over a delivery period up to 30 hours.

Another object of the invention is to provide a dosage form comprising a capsule that comprises an expandable layer, a piston, and a liquid formulation.

Another object of the invention is to provide a dosage form comprising a semipermeable composition coated capsule that comprises a drug-emulsion composition.

Another object of the invention is to provide a process for manufacturing a dosage form which process comprises the steps of adding to a capsule a composition containing a drug, placing a layer that expanse when contacted by an aqueous fluid, closing the capsule, and coating the capsules with a semipermeable coat.

Another object of the invention is to provide a process for manufacturing a dosage form comprising a capsule, which capsule comprises an expandable layer, a piston, and a formulation containing a liquid and a drug.

Other objects, features, aspects and advantages of this invention will be more apparent to those having ordinary skill in the drug delivery art from the accompanying specification taken in conjunction with the drawings and the claims.

BRIEF DESCRIPTION OF DRAWINGS

In the drawing figures, which are not drawn to scale, but are set forth to illustrate operative embodiments of the invention, the drawing figures are as follows.

In the drawing figures and in the specification, like parts in related figures are identified by like numbers. The terms appearing earlier in the specification, and in the description of the drawing figures, as well as embodiments thereof, are further described in the disclosure.

DETAILED DESCRIPTION OF INVENTION

Figure 1:
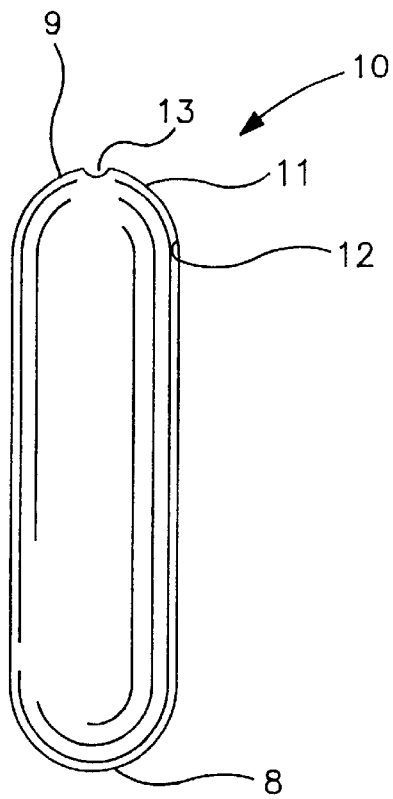
FIG. 1 is a closed, general view of a dosage form provided by the invention.

Turning now to the drawings in detail, which drawings are examples of dosage forms provided by the invention, and which examples are not to be considered as limiting, one example of a dosage form is seen in FIG. 1. In FIG. 1, a dosage form 10, is seen in closed view, comprising a body 11, a wall 12 and passageway 13. Wall 12 surrounds and forms an internal space, not seen in FIG. 1. Dosage form 10 has a lead end 9 with passageway 13 and a bottom end 8.

Figure 2:
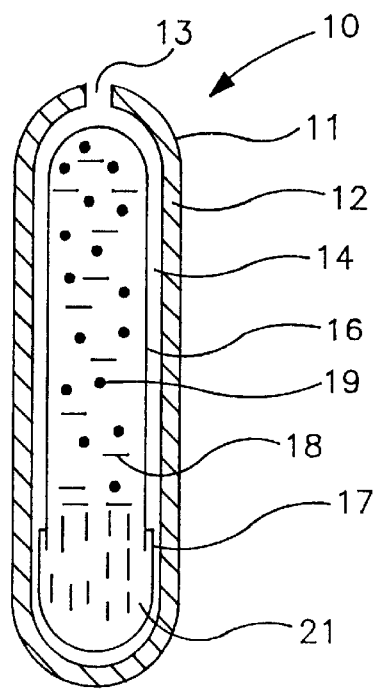
FIG. 2 is an opened view of the dosage form of FIG. 1, wherein in FIG. 2 the dosage form is seen holding and storing a two piece capsule comprising a body section and a cap section for containing a liquid drug formulation.

In drawing FIG. 2, dosage form 10 is seen comprising body 11, wall 12 that surrounds and forms space 14. Wall 12 comprises orifice 13 that connects space 14 with the exterior environment of dosage form 10. Internal space 14 holds and stores a capsule comprising a body section 16 and a cap section 17. The body section 16 is a component receiving section that is filled with a drug 19 or section 16 is filled a composition comprising drug 19 and a pharmaceutically acceptable carrier, 18. The pharmaceutical carrier 18 can be initially dry, or initially wet. A composition 21 comprising an expandable hydrophilic polymer is present in the open end of body 16 and closed by sliding cap 17 over body section 16. In the manufacture wherein body 16 comprises a dry drug 19 composition, a solution or a suspension is formed in the capsule by fluid being imbibed from the environment into the capsule for mixing with the drug in situ.

The capsule is composed of two sections fitted together by slipping or telescoping the cap section over the body section. This provides a closed capsule whose capsule wall surrounds and encapsulates a useful dry drug or liquid drug formulation. The capsule composed of two section defines a hard capsule. Hard capsules are made by dipping stainless steel mold into a bath that contains a solution of a capsule wall forming material to coat the mold with the capsule wall-forming material. The closed and filled capsule is coated next with a composition comprising a semipermeable polymer. The semipermeable composition can be applied to the capsule sections before, or applied after the sections are joined with the final capsule. In another manufacture, the hard two-section capsule can be made with each section having, matched locking rings near their opened end that permits joining and locking the rings together near the overlapping cap and body after filling the capsule. In this manufacture, a pair of matched locking rings are formed into the cap and into the body sections, and these rings provide the locking means for securely holding together the capsule. The capsule can be manually filled with the formulation, or the capsule can be machine filled with the formulation. In the final manufacture, the hard capsule is capsulated with a semipermeable wall on the capsule's exterior surface. The semipermeable wall is permeable to the passage of fluid and substantially impermeable to the passage of drug.

Dosage form 10, in capsule body 16 comprises in one manufacture can initially dry drug formulation, or an initially liquid formulation. The dry formulation comprises drug 19 and a pharmaceutically acceptable carrier 18. The dry drug formulation, when dosage form 10 is in operation in a fluid environment, imbibes fluid into dosage form 10 and self-converts from a dry formulation to a liquid drug formulation. The drug formulation comprises 100 ng to 1500 mg of drugs, or 0.5 wt % to 65 wt % of a drug. Examples of drug include progestins and estrogens. The progestins are represented by a member selected from the group consisting of progesterone, norethindrone, levonorgestrel, norgestimate, northindrone and 17-hydroxyprogesterone. The estrogenic steroids are represented by a member selected from the group consisting of estrogen, estradiol, estradiol valerate, estradiol benzoate, ethinyl estradiol, estrone, estrone acetate, estriol, and estriol triacetate. Representative of drug comprise also diphenedol, meclizine, anisidonie, diphenadione, diphenadione, erythrityl tetranitrate, dizoxin, reserpine, acetazolamide, bendroflumethiazide, chlorpropamide, tolazamide, phenaglycodol, allopurinol, aspirin, aluminum aspirin, metholrexate, acetyl sulfisoxazole, enitabas, and erythromycin.

The dosage form of the invention also delivers pharmacologically active peptides, proteins, proteins anabolic hormones, growth promoting hormones, endocrine system hormones, porcine growth promoting hormone, bovine growth promoting hormone, equine growth promoting hormones, bovine growth promoting hormone, human growth promoting hormone, hormones derived from the pituitary and hypothalamus glands, recombiant DNA, somatropin, gonadotropic releasing hormone, follicle simulating hormone, luteinizing hormone, LH-RH, insulin, colchicine, chorionic gonadotropin, oxytocin, vasopressing adrenocorticothrophic hormone, prolactin, cosyntropin, bypressin, thyroid stimulating hormone, secretin, pancroezymin, enkephalin, glucagon, and like drugs. The drugs are disclosed in U.S. Pat. No. 4,111,201 issued to Theeuwes, and in U.S. Pat. No. 4,951,494 issued to Wong, Theeuwes, and Eckenhoff.

The dry pharmaceutically acceptable carrier for homogeneously blending with 19 to provide a dry drug formulation 19 are represented by a poly(alkylene oxide) of 50,000 to 300,000 weight average molecular weight, an alkali carboyalkylcellulose of 7,500 to 25,000 weight average molecular weight, a copoly (ethylene oxide-propylene oxide) polymer of 4,000 to 25,000 weight average molecular weight, a polysaccharide comprising hydroxyl and carboxyl groups possessing a 250,000 to 400,000 weight average molecular weight, a poly(carboxylated vinyl) polymer, a cyclodextrine, solid polymerized ethylene glycols, a thixotropic gel that flows as a liquid but sets on standing during storage, and a solid poly(ethylene glycol) comprising a molecular weight of 500 to 10,000. The poly(alkylene oxide) polymers are available from the Union Carbide Corporation, Dansbury, Conn.; the poly(ethylene glycols) are disclosed in *Patty's Industrial Hygiene and Toxicology*, by Clayton et al., Vol. 2C, pages 3844–3852, and 3901–3907, (1982) published by Wiley-Interscience Co.; alkalicarboxyalkylcellulose are commercially available from Hercules Co., Lafayette, Calif.; and the carbovinyl polymer are available from B.F. Goodrich Co., Cleveland, Ohio.

The dosage form 10 can comprise 0.5 wt % to 60 wt % of a pharmaceutically acceptable liquid carrier. The pharmaceutically acceptable liquid can comprise a single component or it can comprise more than one component. The pharmaceutically acceptable carrier can comprise a surfactant, that serves to reduce aggregation, reduce interfacial tension between components, enhance the free flow of components, and lessen the incidence of component retention in the dosage form. The drug formulation of this invention, in one embodiment comprises a surfactant that imparts emulsification to the drug formulation. The surfactant can be a member selected from the group consisting of polyoxyethylenated castor oil comprising 9 moles of ethylene oxide, polyoxyethylenated castor oil comprising 15 moles of ethylene oxide, polyoxyethylenated castor oil comprising 20 moles of ethylene oxide, polyoxyethylenated castor oil comprising 25 moles of ethylene oxide, polyoxyethylenated castor oil comprising 40 moles of ethylene oxide, polyoxyethylenated castor oil comprising 52 moles of ethylene oxide, polyoxyethylendated sorbitan monopalmitate comprising 20 moles of ethylene oxide, polyoxyethylenated sorbitan monostearate comprising 4 moles of ethylene oxide, polyoxyethylenated sorbitan tristearate comprising 20 moles of ethylene oxide, polkyoxyethylenated stearic and comprising 8 moles of ethylene oxide, polyoxyethylene lauryl ether, polyoxyethylenated stearic acid comprising 40 moles of ethylene oxide, polyoxyethylenated stearic acid comprising 30 moles of ethylene oxide, polyoxyethylenated stearyl alcohol comprising 2 moles of ethylene oxide, and polyoxyethylenated oleyl alcohol comprising 2 moles of surfactant. The surfactants are available from Atlas Chemical Industries, Wilmington, Del.; Drew Chemical Corp., Boonton, N.J.; and GAF Corp., New York, N.Y.

The drug formulation can comprise an oil phase, blended with the drug and the surfactant. The oil phase comprises a pharmaceutically acceptable oil that is non-polar in nature, or non-polar after synthesis. The oil can be an edible liquid such as a non-polar ester of an unsaturated fatty acid, or mixtures of such esters can be utilized for this purpose. The oil can be vegetable, mineral, animal, or marine in origin. Examples of non-toxic oils comprise a member selected from the group consisting of peanut oil, cottonseed oil, sesame oil, olive oil, corn oil, almond oil, mineral oil, castor oil, coconut oil, palm oil, cocoa butter oil, safflower oil, a mixture of moni- and di-gylcerides of 16 to 18 carbon atoms, unsaturated fatty acids, fractionated trigylcerides derived from coconut oil, and fractionated liquid triglycerides derived from short chain 10 to 15 carbon atom fatty acid, acetylated monoglycerides, acetylated triglycerides, olein known also as glycerol trioleate, palmitin known also as glycerol tripalmitate, stearin known also as glycerol tristearate, lauric acid hexylester, olein acid oleylester, glycolyzed ethoxylated, glyceride of natural oils, branched fatty acids with 13 molecules of ethylene oxide, olein acid decylester, and branched liquid fatty acids.

The pharmaceutically acceptable liquid carrier also embraces liquid prepolymers, emulsions of the single phase and two phase types such as oil-in-water and water-in-oil, emulsions of castor oil in aqueous solution of pigskin gelatin, emulsion of gum arabic, oils with emulsifiers such as mono- or di-gylcerides of a fatty acid, and lecithin and a fatty acid ester. The concentration of oil, or oil derivatives in the drug liquid formulation is 1 wt % to 50 wt %, with the wt % of all components in the drug liquid formulation equal to 100 wt %. The oils are disclosed in *Pharmaceutical Sciences* by Remington, 17$^{th}$ Ed., pg. 403–405 (1985) published by Mack Publishing Co., in *Encyclopedia of Chemistry*, by Van Nostrand Reinhold Co., 4$^{th}$ Ed., pg. 644 to 645 (1984) published by Van Nostrand Co.; in U.S. Pat. No. 4,259,323 issued to Ranucci; and in U.S. Pat. No. 3,905,360 issued to Zaffaroni.

Dosage form 10 in capsule body 16 comprises an expandable composition 21 that expands in the presence of imbibed aqueous and biological fluids. Body 16 comprising expandable composition 21 is closed by cap 17, to provide a closed capsule in dosage form 10. Composition 21 is an expandable push driving force that acts in cooperation with dosage form 10 for delivering drug 19 from dosage form 10. Composition 21 exhibits fluid imbibing and/or absorbing properties. Composition 21 comprises a hydrophilic polymer that can interact with water and aqueous biological fluids and then swell or expand. The hydrophilic polymers are known also as osmopolymers, osmogels and hydrogels, and they exhibit a concentration gradient across wall 12, whereby they imbibe fluid into dosage form 10. Representative of hydrophilic polymers are poly(alkylene oxide) of 1,000,000 to 10,000,000 weight-average molecular weight including poly (ethylene oxide), and an alkali carboxymethylcellulose of 10,000 to 6,000,000 weight average molecular weight including sodium carboxymethylcellulose. Composition 21 comprises 10 mg to 425 mg of osmopolymer. Composition 21 can comprise 1 mg to 50 mg of a poly(cellulose) of a member selected from the group consisting of hydroxyethylcellulose, hydroxyproylcellulose, hydroxypropylmethylcellulose, and hydroxypropylbutylcellulose. Composition 21 comprises 0.5 mg to 175 mg of an osmotically effective solute, known also as osmotic solute and osmagent, that imbibe fluid through wall 12 into dosage form 10. The osmotically effective solutes are selected from the group consisting of a salt, acid, amine, ester and carbohydrate. Representative osmagents are selected from the group consisting of magnesium sulfate, magnesium chloride, potassium sulfate, sodium sulfate, lithuim sulfate, potassium acid phosphate, mannitol, urea, inositol, magnesium succinate, tartaric acid, sodium chloride, potassium chloride, and carbohydrates such as raffinose, sucrose, glucose, lactose, and sorbitol. Composition 21 optionally comprises 0 wt % to 3.5 wt % of a colorant, such as ferric oxide. The total weight of all components in composition 21 is equal to 100 wt %.

Dosage form 10 comprises a wall 12 that surrounds the internal capsule. Wall 12 comprises a composition permeable to the passage of fluid, aqueous and biological fluid, present in environment of use, in animal including a human, and wall 12 is substantially impermeable to the passage of drug 19, and the components of emulsion formulation 19. Wall 12 is nontoxic, and it maintains its physical and chemical integrity during the drug delivery device of dosage form 10. Representative of materials for forming wall 12, include semipermeable polymers, semipermeable homopolymers, semipermeable copolymer, and semipermeable terpolymers. The polymers comprise polymers including cellulose esters, cellulose ethers, and cellulose ester-esters. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substitute with groups such as acyl, alkanoyl, alkenoyl, aroyl, alkyl, alkoxy, halogen, carboalkyl, alkylcarbamate, alkylcarbonate, alkylsulfonate, alkylsulfamate, and semipermeable polymer forming groups.

The semipermeable materials typically include a member selected from the group consisting of cellulose acylate, cellulose diacylate, cellulose triacetate, cellulose acetate, cellulose diacetate, cellulose triacetate, mono-, di- and tri-cellulose alkanylates, mono-, di-, and tri-alkenylates, mono-, di-, and tri-aroylates, and the like. Examplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%; and the like. More specific cellulosic polymers include cellulose proprionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acette butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, celluloser acetate succinate, cellulose propionate succinate, cellulose acetate octanoate, cellulose valerate palmitate, cellulose acetate heptonate, cellulose valerate palmitate, cellulose acetate heptonate, and the like. Semipermeable polymers are known in U.S. Pat. No. 4,077,407, and they can be made by procedures described in *Encyclopedia of Polymer Science and Technology*, Vol. 3, pages 325 to 354, 1965, published by lnterscience Publishers, Inc., New York.

Additional semipermeable polymers include cellulose acetaldehyde dimethyl acetate; cellulose acetate ethylcarbonate; cellulose acetate methylcarbamate; cellulose dimethylaminoacetate; semipermeable polyamides; semipermeable polyurethanes; semipermeable sulfonated polystyrenes; cross-linked, selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable polystyrene derivatives; semipermeable poly(sodium styrenesulfonate); semipermeable poly(vinylbenzyltrimethyl)ammonium chloride; semipermeable polymers exhibiting a fluid permeability of 10 to 10 (cc.mil/cm.hr.atm) expressed as per atmosphere of hydrostatic or osmotic pressure difference across a semipermeable wall. The polymers are known to the art in U.S. Pat. Nos. 3,845,770; 3,916,899; and 4,160,020, and in *Handbook of Common Polymers*, by Scott, J. R. and Ross, W. J., 1971, published by CRC Press, Cleveland, Ohio.

Figure 3:
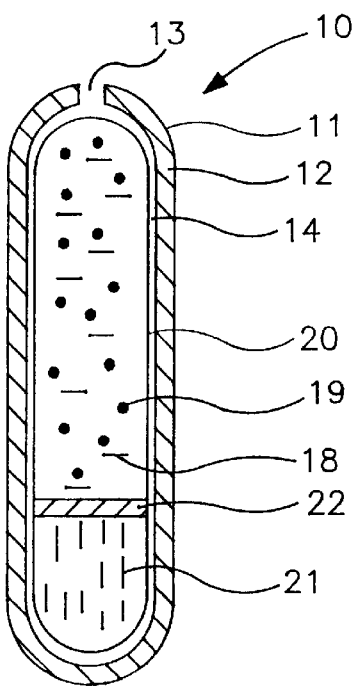
FIG. 3 is an opened view of the dosage form by FIG. 1, wherein in FIG. 3 the dosage form is seen containing a capsule made as a unit piece which capsule contains a liquid drug formulation.

Drawing FIG. 3 illustrates another dosage form 10 provided by this invention. In FIG. 3, dosage form 10 comprises a body 11, comprising wall 12 with a passageway 13. Wall 12 surrounds and defines internal compartment 14 housing internal capsule 20. Internal capsule 20 in its final manufacture comprises a one piece capsule that distinguishes capsule 20 from the two piece capsule presented above. Capsule 20 comprises a composition comprising drug 19 and pharmaceutically acceptable carrier 18 as presented above. Capsule 20 comprises also composition 20, the expandable composition presented above. Capsule 20 in drawing FIG. 3 comprises a movable piston 22. The movable piston 22, moves or slides in response to pressure generated inside capsule 20. The piston is positioned between and in contacting relation with the liquid formulation and expandable composition 21. The piston serves to reduce diffusion and/or migration between the liquid drug formulation and the expandable composition, thereby maintaining the concentration of the liquid formulation, and the piston also prevents interaction between the liquid formulation and the expandable compositioin, thereby maintaining the stability of the liquid formulation.

Dosage form 10 in operation imbides fluid through wall 12 causing composition 19 to expand and apply pressure against piston 22. This applied pressure moves piston 22 towards passageway 13 whereby the liquid drug formulation is pushed through passageway into the environment of use. Representative of materials for manufacturing movable piston 22 comprise a member selected from the group consisting of a wax, petroleum wax, an ester of a high molecular weight fatty acid with a high molecular weight alcohol, a piston formed of an olefin polymer, a condensation polymer, rubber, organosilicon, high density polyethylene, high density polypropylene, and piston forming materials impermeable to fluid.

In FIG. 3, capsule 20 is surrounded and/or coated by semipermeable wall 12 presented above. Capsule 20 in FIG. 3 comprises a sealed construction encapsulating the drug formulation, the piston, and the expandable composition. The capsule is made by various processes including the plate process, the rotary die process, the reciprocating die process, and the continuous process. The place process uses a set of molds. A warm sheet of a prepared capsule lamina-forming material is laid over the lower mold and the formulation poured on it. A second sheet of the lamina-forming material is placed over the formulation followed by the top mold. The mold set is placed under a press and a pressure applied, with or without heat to form a unit, capsule. The capsules are washed with a solvent for removing excess agent formulation from the exterior of the capsule, and the air-dried capsule is encapsulated with a semipermeable wall.

The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be capsuled flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein the capsules are simultaneously filled, shaped, hermetically sealed and cut from the sheets of lamina-forming materials. The sealing of the capsule is achieved by mechanical pressure on the die rolls and by heating of the sheets of lamina-forming materials by the wedge. After manufacture, the agent formulation-filled capsules are dried in the presence of forced air, and a semipermeable lamina capsuled thereto, by processes described hereafter.

The reciprocating die process produces capsules by leading two films of capsule lamina-forming material between a set of vertical dies. The dies as they close, open, and close perform as a continuous vertical plate forming row after row of pockets across the film. The pockets are filled with agent formulation, and as the pockets move through the dies, they are sealed, shaped and cut from the moving film as capsules filled with agent formulation. A semipermeable capsulating lamina is coated thereon to yield the capsule. The continuous process is a manufacturing system that also uses rotary dies with the added feature that the process can successfully fill active agent in dry power form into a soft capsule, in addition to encapsulating liquids. The filled, capsule of the continuous process is encapsulated with a semipermeable polymeric material to yield the capsule. Procedures for manufacturing unit capsules are disclosed in U.S. Pat. No. 4,627,850 issued to inventors Deters, Theeuwes, Mullins, and Eckenhoff.

Figure 4:
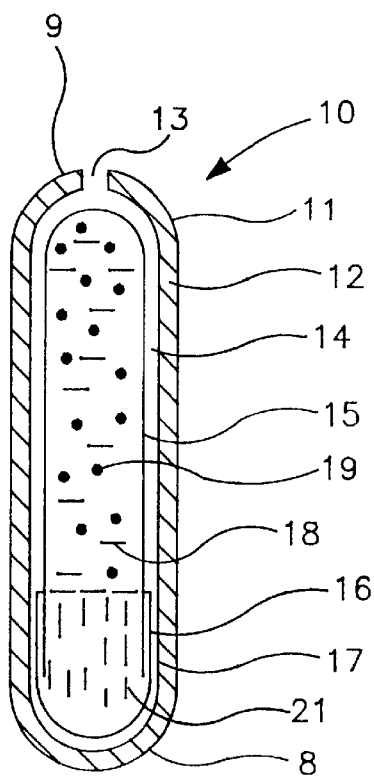
FIG. 4 is an opened view of the dosage form of FIG. 1 comprising a capsule comprising a body section and a cap section comprising a drug formulation and an osmotic composition, with the capsule surrounded by a semipermeable wall with an exit passageway.

Drawing FIG. 4 illustrates another dosage form 10 provided by the invention. In drawing FIG. 4, dosage form 10 comprises lead end 9, trailing end 8, capsule cap 17, drug 19 and carrier 18 in capsule body 16, expandable composition 21 in capsule body 16 closed by capsule cap 17. The components comprising FIG. 4 were presented above, and that presentation is incorporated herein.

In drawing FIG. 4, dosage form 10 comprises wall 12 made from an injection-moldable composition by an injection-molding techniques. Injection-moldable compositions provided for injection-molding into wall 12 comprise a thermoplastic polymer, or the compositions comprise a mixture of thermoplastic polymers and optional injection-molding ingredients. The thermoplastic polymer that can be used for the present purpose comprise polymers that have a low softening point, for example, below 200° C., preferably within the range of 40° C. to 180° C. The polymers, are preferably synthetic resins, for example, linear polycondensation resins, condensation polymerized resins, addition polymerized resins, such as polyamides, resins obtained from diepoxides and primary alkanolamines, resins of glycerine and phthalic anhydrides, polymethane, polyvinyl resins, polymer resins with end-positions free or esterified carboxyl or carboxamide groups, for example with acrylic acid, acrylic amide, or acrylic acid esters,, polycaprolactone, and its copolymers with dilactide, diglycolide, valerolactone and decalactone, a resin composition comprising polycaprolactone and polyalkylene oxide, and a resin composition comprising polycaprolactone, a polyalkylene oxide such as polyethylene oxide, poly(cellulose) such as poly((hydroxypropylmethylcellulose), poly(hydroxyethylmethylcellulose), poly(hydroxyethylcellulose), and poly(hydroxypropylkcellulose). The membrane forming composition can comprises optical membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another embodiment comprises 10% to 99% of a thermoplastic polymer and 1% to 70% of a different polymer with the total equal to 100%. The invention provides also a thermoplastic polymer composition comprising 1% to 98% of a first thermoplastic polymer, 1% to 90% of a different, second polymer and 1% to 90% of a different, third polymer with all polymers equal to 100%. Representation composition comprises 20% to 90% of thermoplastic polycaprolactone and 10% to 80% of poly(alkylene oxide); a composition comprising 20% to 90% of poly(alkylene oxide); a composition comprising 20% to 90% polycaprolactone and 10% to 60% of poly(ethylene oxide) with the ingredients eqal to 100%; a composition comprising of 10% to 97% polycaprolactone, 10% to 97% poly(alkylene oxide), and 1% to 97% of poly(ethylene glycol) with all ingredients equal to 100%; a composition comprising 20% to 90% polycaprolactone and 10% to 80% of polyethylene glycol 40 stearate (Myrj 525) with all ingredients equal to 100%; and a composition comprising 1% to 90% polycaprolactone, 1% to 90% poly(ethylene oxide), 1% to 90% poly(hydroxypropylcellulose) and 1% to 90% poly(ethylene glycol) with all ingredients equal to 100%. The percent, expressed is weight percent, wt %.

In another embodiment of the invention, a composition for injection-molding to provide a membrane is prepared by blending a composition comprising a polycaprolactone 63 wt %, polyethylene oxide 27 wt %, and polyethylene glycol 10 wt % in a conventional mixing machine, such as a Moriyama® Mixer at 65° C. to 95° C., with the ingredients added to the mixer in the following addition sequence, polycaprolactone, polyethylene oxide and polyethylene glycol. All the ingredients were mixed for 135 minutes at a rotor speed of 10 to 20 rpm. Next, the blend is fed to a Baker Perkins Kneader® extruder at a 80° C. to 90° C., at a pump speed of 10 rpm and a screw speed of 22 rpm, and then cooled to 10° C. to 12° C. to reach a uniform temperature. Then, the cooled extruded composition is fed to an Albe Pelletizer, converted into pellets at 250° C. and a length of 5 mm. The pellets next are fed into an injection-molding machine, an Arburg Allrounder® at 200° F. to 350° F. (93° C. 177° C.), heated to a molten polymeric composition, and the liquid polymer composition forced into a mold cavity at high pressure and speed until the molded is filled and the composition comprising the polymers are solidified into a preselected shape. The parameters for the injection-molding consists of a band temperature through zone 1 to zone 5 of the barrel of 195° F. (91° C.) to 375° F. (191° C.), an injection-molding pressure of 1818 bar, a speed of 55 cm$^3$/s, and a mold temperature of 75° C. The injection-molding compositions and injection-molding procedures are disclosed in U.S. Pat. No. 5,614,578 issued to Dong, Wong, Pollock, and Ferrari.

The expression passageway as used herein denotes means and methods suitable for releasing the useful, active drug emulsion formulation from the dosage form. The expression includes passage way, aperture, hole, bore, pore and the like through the semipermeable walls. The orifice can be formed by mechanical drilling, laser drilling, or by eroding an erodible element, such as a gelatin plug, a pressed glucose plug, to yield the orifice, when the dosage form is in the environment of use. In an embodiment, the orifice in wall 12 is formed in the environment of use in response to the hydrostatic pressure generated in dosage form 10. In another embodiment, the dosage form 10 can be manufactured with two or more orifices in spaced-class relation for delivering drug 20 from dosage form 10. The orifice 13, can be formed by mechanical rupturing of wall 12 during operation of dosage form 10. A detailed description of orifices and the maximum and minimum dimensions of an orifice are disclosed in U.S. Pat. Nos. 3,845,770 and 3,916,899 both issued to inventors Theeuwes and Higuchi.

EXAMPLES OF THE INVENTION

The following examples are illustrative of the present invention, and the examples should not be considered as limiting the scope of this invention in any way, as these examples and other equivalents thereof will become apparent to those versed in the drug dispensing art in the light of the present disclosure, and the accompanying claims.

Example 1

A dosage form is manufactured for dispensing a beneficial drug orally to the gastrointestinal tract as follows: first, a composition comprising expandable properties is prepared by adding 58.7 wt % sodium carboxymethylcellulose is added to the bowl of a fluid bed granulator. Next, 30 wt % of sodium chloride, 5.0 wt % hydroxyproplymethylcellulose of 11,300 molecular weight and 1 wt % red ferric oxide are added to the fluid bed granulator. In a separate container, a granulating solution is prepared by dissolving 5.0 wt % hydroxypropylcellulose of 40,000 molecular weight in purified water. Then, the granulating solution is sprayed onto the fluidized powders until all the solution is applied and the powders are granular. Next, 0.25 wt % of magnesium stearate is blended with the granular. The composition is compressed into a tablet with a conventional tablet press, as follows: two hundred and fifty mg of the composition are added to a $\%_{32}$ inch punch, tamped and then compressed under a force of about 1 metric ton into a expandable osmogel tablet.

Next, a drug formulation is prepared as follows: 50 wt % of progesterone, 33.4 wt % of polyoxyl 35 castor oil available as Cremophor EI from BASF Corp., Mount Olive, N.J., and 16.5 wt % of acetylated monoglyceride available as Myvacet available from Eastman Corp., Kingsport, Tenn., are mixed homogeneously using a standard homogenizer.

Then, a capsule comprising a gelatin wall, size 0, is separated into two segments, its body and its cap. Then, 600 mg of the drug formulation is filled into the body of the capsule followed by an osmotic tablet inserted into an injection-molded wall with the osmotic tablet facing the bottom of the injection-molded walled housing. Finally, the walls are crimped at about 68° C. to provide an exit passageway of 155 mil (3.875 mm).

Example 2

The procedure of Example 1 is repeated in the example for providing the dosage form except a piston is place in contact with the drug formulation followed by the expandable osmogel tablet prior to forming the exit passageway in the injection-molded wall.

Example 3

The procedure of Example 1 is repeated in this example for providing the dosage form except in this example a piston is placed in contact with the drug formulation, followed by the expandable osmogel tablet, with the body of the capsule capped by the cap of the capsule prior to forming the exit passageway in the outer injection-molded wall.

Example 4

The procedure of Example 1 is followed for providing the dosage form, except in this example the drug formulation comprises 50 wt % progesterone, 37.5 wt % polyoxyl 34 castor oil, and 12.5 wt % acetylated monoglyceride.

Example 5

The procedure of Example 1 is repeated in this example for providing a dosage form wherein the drug formulation comprises 50 wt % progesterone, 25 wt % polyoxyl 35 castor oil and 25 wt % acetylated monoglyceride.

Example 6

The procedure of Example 1 is repeated in this example, except herein the drug formulation comprises 50 wt % progesterone and 50 wt % polyoxyl 35 castor oil.

Example 7

The procedure of Example 2 is followed in this example for providing the dosage form, except in this example the drug formulation comprises the drug formulation and the expandable osmogel tablet, the capsule body is closed with the capsule cap, prior to being placed in the injection-molded wall provided with an exit passageway.

Example 8

A dosage form is manufactured for dispensing a beneficial drug to the gastrointestinal tract of a human as follows: first, an expandable composition is prepared in a fluid bed granulator. The expandable composition comprises 30 wt % sodium chloride screened through a 20 mesh screen added to the granulator bowl, followed by 58.75 wt % polyethylene oxide of 2,000,000 molecular weight. Then, 5 wt % hydroxypropylmethylcellulose possessing a 9,200 molecular weight and 1% red ferric oxide is added to the granulator bowl. In a separate mixer, a granulation solution is prepared by dissolving 5 wt % hydroxypropylcellulose in purified water. Then, the granulating solution is sprayed onto the fludized powders in the granulator until all the solution is applied and the powders are granular. Next 0.25 wt % magnesium stearate is blended with the just prepared granules. The granules are compressed into a tablet-shaped layer comprising 250 mg of granules in a $\%_{32}$ inch punch, tamped, and then compressed under a force of 1 metric ton to provide the osmogel driving tablet.

Next, a drug formulation is prepared as follows: first 50 wt % of microfluidized acylovir, 12.5 wt % polyoxyethylene 20 stearate, 25 wt % polyoxyl 35 castor oil available as Cremophor EI® from BASF Corp., Mount Olive, N.J., and 12.5 wt % polyoxyl 40 stearate commercially available as Myrj® 52 from ICI Inc., Wilmington, Del. are blended in a homogenizer to provide a homogenous blend.

Next, a capsule made of pharmaceutically gelatin is separated into its body and cap. The body is first charged with the drug formulation, followed by a piston formed of high density polyethylene, which is followed by the expandable composition. The filled capsule body is closed with the gelatin cap.

Figure 5:
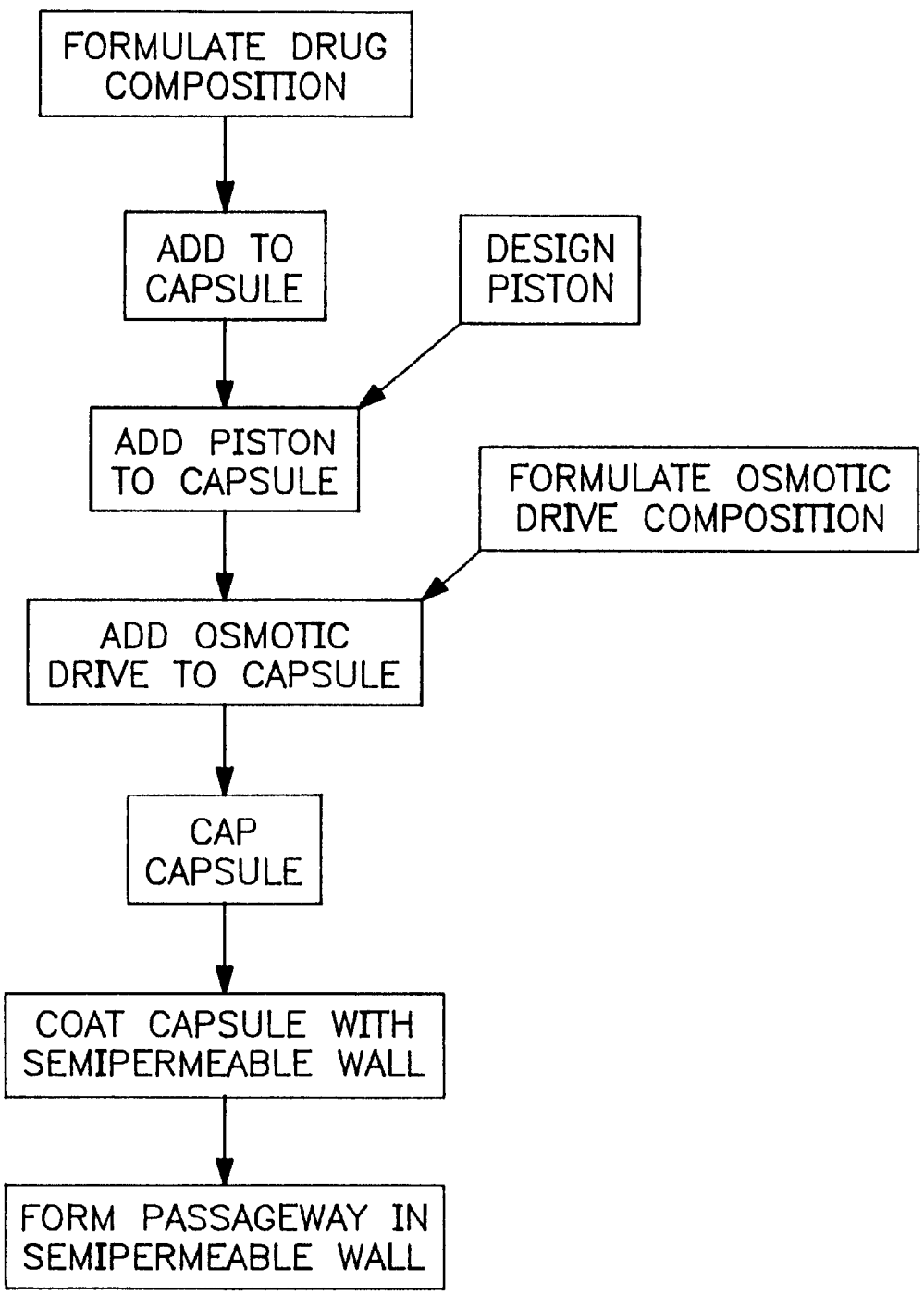
FIG. 5 depicts a flow diagram for manufacturing a dosage form of the invention.

Next, the assembled capsule is coated with a semipermeable wall is applied from a wall forming composition. Then wall-forming composition comprises 85 wt % cellulose acetate comprising a 39.8% acetyl content, and 15 wt % polyethylene glycol 3350. The wall forming composition is dissolved in acetone/methanol (80/20 wt/wt) cosolvent to make 4% solid solution. The solution is sprayed onto the capsule in an air suspension coater. The semipermeable wall coated capsules are dried in an oven at 50° C. and 50° relative humidity for 1 day to remove all solvents. Then, a passageway is drilled in the semipermeable wall to provide the drug dispensing dosage form. Accompanying FIG. 5 depicts a flow chart of a process for manufacturing the dosage form of the invention.

Method of Using the Dosage Form

The invention provides also a method of administering a drug to a human patient. The method comprises orally admitting into the gastrointestinal tract of a human the dosage form provide by the invention. The method comprises the steps of (1) admitting orally the dosage form into the gastrointestinal tract, which dosage form comprises: (a) a wall for imbibing an external fluid, aqueous-biological, through the wall into the dosage form, which wall surrounds; (b) a capsule, the capsule comprising; (c) a drug formulation, a piston and an osmotic driving force; and (d) an exit in the semipermeable wall; (2) permitting imbibed aqueous fluid to dissolve the gelatin capsule; (3) letting imbibed fluid mix with the drug composition to form a dispensable composition; (4) letting imbibed fluid be absorbed by the osmotic driving composition thereby causing the composition swell, expand and push the drug composition through the passageway at a controlled rate over a sustained-release period up to twenty-four hours.

Inasmuch as the foregoing specification comprised representative embodiments of the invention, it is understood that changes, modifications and variations can be made herein, in accordance with the inventive principles disclosed, without departing from the scope of the invention.

We claim:

1. A process for providing a dosage form, said process comprising the following steps:
   (a) blending an osmopolymer, an osmagent and a hydroxypropylalkylcellulose to provide an osmotic composition;
   (b) blending a hydroxyalkylcellulose with a fluid to provide a granulating fluid;
   (c) spraying the granulating fluid onto the osmotic composition;
   (d) blending a drug and surfactant to form a liquid drug formulation wherein the liquid drug formulation is delivered at a sustained-release rate over an extended period of time:
   (e) adding the liquid drug formulation into a capsule;
   (f) adding the osmotic composition into the capsule;
   (g) closing the capsule;
   (h) inserting the capsule into a wall housing comprised of an injection-moldable composition having a closed bottom and an open mouth; and
   (i) crimping the wall to close the mouth while maintaining an orifice in the dosage form.

2. The process for providing the dosage form of claim 1, wherein the housing is closed with a snap-in closure that maintains an orifice in the dosage form.

3. The process for providing the dosage form according to claim 1, wherein the liquid drug formulation is prepared as step (a).

4. The process for providing the dosage form according to claim 1, wherein step (f) is step (e).

5. A process for providing a dosage form, wherein the process comprises the following steps:
   (a) formulating a liquid drug formulation comprising a drug and a pharmaceutically acceptable carrier;
   (b) formulating an expandable composition comprising a homopolymer and an osmotically effective solute;
   (c) adding the therapeutic composition to a capsule;
   (d) adding the expandable composition to the capsule;
   (e) coating the capsule with an injection-moldable composition to form a wall; and
   (f) providing an exit means in the wall in communication with the liquid drug formulation for releasing the liquid drug formulation at a sustained-release rate over an extended period of time.

* * * * *